(12) United States Patent
Noren et al.

(10) Patent No.: US 6,915,162 B2
(45) Date of Patent: Jul. 5, 2005

(54) IMPLANTABLE MEDICAL DEVICE FOR MEASURING VENTRICULAR PRESSURE

(75) Inventors: Kjell Noren, Solna (SE); Charlotte Kjellmann, Stockholm (SE); Kenth Nilsson, Akersberga (SE); Sven-Erik Hedberg, Kungsängen (SE)

(73) Assignee: St. Jude Medical AB, Järfälla (SE)

( * ) Notice: Subject to any disclaimer, the term of this patent is extended or adjusted under 35 U.S.C. 154(b) by 319 days.

(21) Appl. No.: 10/002,496

(22) Filed: Nov. 15, 2001

(65) Prior Publication Data

US 2002/0058969 A1 May 16, 2002

(30) Foreign Application Priority Data

Nov. 16, 2000 (SE) .............................................. 0004224

(51) Int. Cl.[7] .............................. A61N 1/365; A61B 5/04
(52) U.S. Cl. ........................ 607/23; 600/485; 600/513
(58) Field of Search ........................... 607/17, 18, 19, 607/21, 23, 25, 6; 600/513, 485

(56) References Cited

U.S. PATENT DOCUMENTS

| | | | |
|---|---|---|---|
| 4,774,950 A | * 10/1988 | Cohen | 607/6 |
| 5,040,540 A | 8/1991 | Sackner | |
| 5,083,563 A | * 1/1992 | Collins | 607/4 |
| 5,105,810 A | 4/1992 | Collins et al. | |
| 5,163,429 A | 11/1992 | Cohen | |
| 5,324,326 A | 6/1994 | Lubin | |
| 5,368,040 A | 11/1994 | Carney | |
| 5,626,623 A | 5/1997 | Kieval et al. | |
| 5,743,267 A | * 4/1998 | Nikolic et al. | 600/483 |
| 5,843,135 A | 12/1998 | Weijand et al. | |

FOREIGN PATENT DOCUMENTS

EP 0347708 * 12/1989 ................. 607/17

* cited by examiner

Primary Examiner—Jeffery R. Jastrzab
(74) Attorney, Agent, or Firm—Schiff Hardin LLP

(57) ABSTRACT

An implantable medical device has a pressure sensing arrangement to measure right ventricular pressure of a heart including a pressure sensor adapted to be positioned in the right ventricle of the heart, to measure the pressure and to generate a pressure signal in response to the measured pressure. The pressure sensing arrangement also has a pressure signal processor and a timing unit. The processor determines from the pressure signal, using diastolic timing signals from the timing unit based on the pressure signal identifying the diastolic phase, a diastolic pressure signal representing the ventricular pressure only during the diastolic phase of the heart cycle.

8 Claims, 7 Drawing Sheets

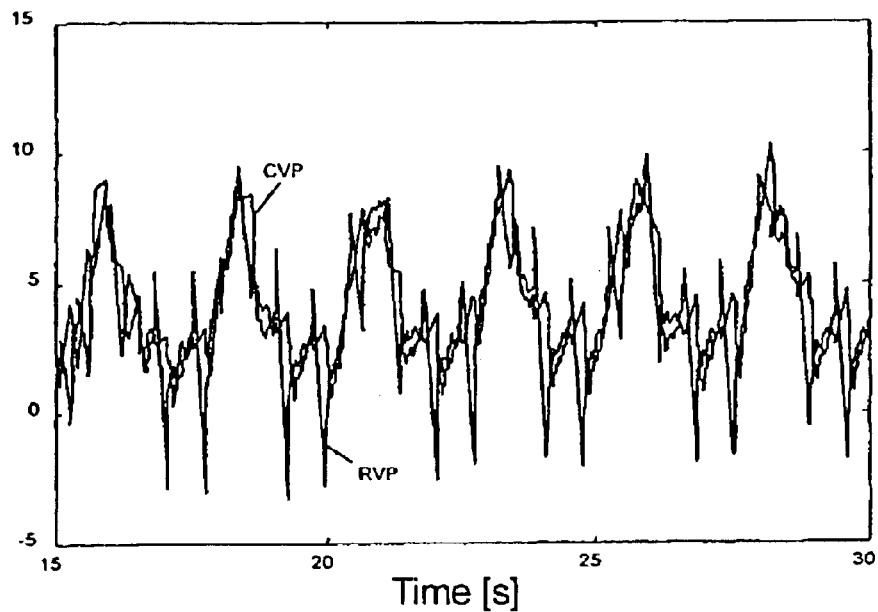
FIG. 6a
FIG. 6b
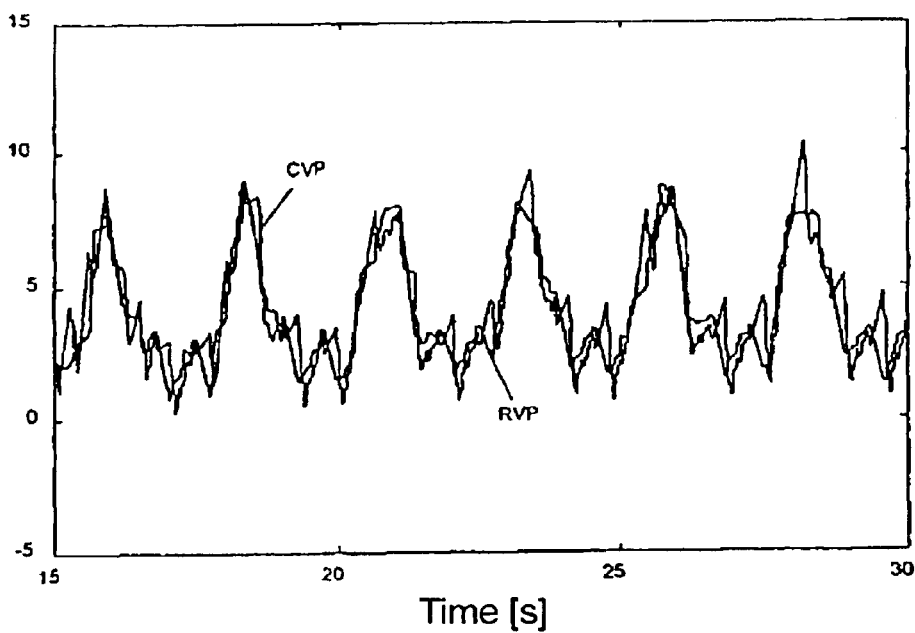

IMPLANTABLE MEDICAL DEVICE FOR MEASURING VENTRICULAR PRESSURE

BACKGROUND OF THE INVENTION

1. Field of the Invention

The present invention relates to an implantable medical device of the type used for measuring ventricular pressure in a subject.

2. Description of the Prior Art

The pressure of the blood entering the heart is of great interest. All the blood from the veins in the body enters the heart into the right atrium. This represents 95% of the total venous blood volume, the remaining 5% of the volume enter from coronary sinus, which is the return from the hearts own blood supply. The pressure in the vena cava, the large vein just outside the heart, is called central venous pressure (CVP). The average level of CVP is just a few mmHg but because the vena cava is very elastic (has high compliance), a small change in pressure indicates that a large volume of blood is involved. The CVP is therefore of great interest because it is an indicator of the blood volume that flows through the veins and enters the heart. The pressure in the vena cava will increase if the heart beats too weakly. The increase indicates that the blood is backed up in the veins. The normal response from the heart in this situation is to beat faster and/or increase the stroke volume. There is also another factor that can cause an increase in the CVP resulting from the increase in blood volume when a person lies down, e.g. when he goes to bed at night. The response of the heart is the same as above, i.e. to beat faster and/or increase the stroke volume.

In U.S. Pat. No. 5,040,540 different methods of measuring central venous pressure are disclosed. To obtain a valid central venous pressure a measurement catheter could be placed within the right atrium or one of the great veins of the thorax (e.g. the superior vena cava, the innominate vein or the subclavian vein).

Measuring in the right atrium should be avoided according to U.S. Pat. No. 5,040,540 due, inter alia, to the risk of perforation of the atrial wall.

Pressure sensors adapted to be inserted inside a heart are well known in the art, see e.g. U.S. Pat. Nos. 5,843,135 and 5,324,326.

In U.S. Pat. 5,843,135 a piezoelectric pressure transducer is arranged in a patient's heart, e.g. in the right ventricle or right atrium.

U.S. Pat. No. 5,324,326 discloses a pressure sensing pacing lead having a distal pressure sensor for sensing hemodynamic pressure within the heart. The pressure sensor has an integrated circuit chip having a layer of piezoresistive material and a non-conductive base member.

During diastole, the filling phase of the heart cycle, the tricuspid valve, which is the valve between the right atrium and the right ventricle of the heart, is open. A consequence thereof is that pressure measured in the right ventricle during diastole also reflects the pressure in the right atrium and also the pressure close to the heart in the veins transporting blood into the right atrium (superior vena cava etc.).

U.S. Pat. No. 5,163,429 discloses a hemodynamically responsive system for treating a malfunctioning heart. A signal is developed that is representative of pressure sensed at a site in a patient's circulatory system. This signal may represent e.g. short-term mean right ventricular pressure, mean central venous pressure, right ventricular systolic pressure, or right ventricular diastolic pressure.

In U.S. Pat. No. 5,163,429 as well, a signal representative of the right ventricular systolic pressure is determined by detecting a real time representation of peak pressure provided that a zero slope condition follows a positive slope. The thus detected peak pressure is shifted into a shift register for further evaluation. Following the determination of the right ventricular systolic pressure it is briefly described that similar circuitry also may be used to determine right ventricular diastolic pressure by using a negative slope detector instead of a positive slope detector. According to the system in U.S. Pat. No. 5,163,429 only a single pressure value (the minimum value) is determined each heart cycle during the diastolic phase. The determined pressure value is then used to obtain short-term or long-term signal representations of right ventricular diastolic pressure.

U.S. Pat. No. 5,368,040 discloses an apparatus and method for monitoring and measuring a number of hemodynamic variables from a single, chronically implanted absolute pressure sensor.

In this known device the first and second derivatives of the pressure signal are used together with the ECG signal to identify start and end points of the systolic and diastolic intervals, respectively.

As shown in FIG. 1 in U.S. Pat. No. 5,368,040 the PA systolic pressure is determined by feeding the sensed RV pressure sensor output into a sample and hold circuit that is enabled by the sensing of the R-wave. The systolic pressure is then latched when dP/dt goes negative. The latched value is then held until the next R-wave is sensed.

One drawback with the apparatus described in U.S. Pat. No. 5,368,040 is that information related to the internal EGM signal is required in order to identify specific portions of the heart cycle which renders the apparatus complicated.

A general drawback with the above-described prior art systems is that only limited information of the pressure variation is obtained. No continuous pressure curve of the diastolic pressure is determined.

SUMMARY OF THE INVENTION

An object of the present invention is to provide an implantable medical device which performs a pressure measurement that allows minor pressure variations to be detected as well by using a technically less complicated apparatus.

The above object is achieved in accordance with the principles of the present invention in an implantable medical device having a pressure sensor adapted to be positioned in the right ventricle of the heart to measure the right ventricular pressure and to generate a pressure signal dependent on the measured pressure, a timing unit, supplied with the pressure signal, which identifies the diastolic phase of the heart dependent on the pressure signal, and a processor, also supplied with the pressure signal which determines from the pressure signal, using diastolic timing signals from the timing unit, a diastolic pressure signal which represents the ventricular pressure only during the diastolic phase of the heart cycle.

According to the invention a pressure sensor arranged in the right ventricle of the heart might also be used, in addition to measuring the right ventricular pressure, to determine a value representing the central venous pressure in the vena cava.

It is a great advantage to be able to determine the central venous pressure without placing a sensor in the vena cava. It is considered more difficult and thus more expensive to directly measure the pressure in a great vein, e.g. the vena cava, because an electrode lead with a pressure sensor becomes more complicated and possibly also more difficult to arrange.

A pressure sensor used in a pacemaker is conventionally arranged on an electrode lead adapted to be place inside the heart, e.g. in the right ventricle or in the right atrium.

The present invention makes it possible to extend the applicability of a pressure signal obtained in the right ventricle or atrium.

According to a preferred embodiment of the present invention the obtained diastolic pressure signal is processed in a median filter in order to achieve a smooth transition between of the curve obtained from diastolic phases from adjacent heart cycles.

DESCRIPTION OF THE DRAWINGS

FIGS. 6a and 6b show CVP and RVP tracings in order to illustrate the benefits of the median filter.

DESCRIPTION OF THE PREFERRED EMBODIMENTS

Figure 1:
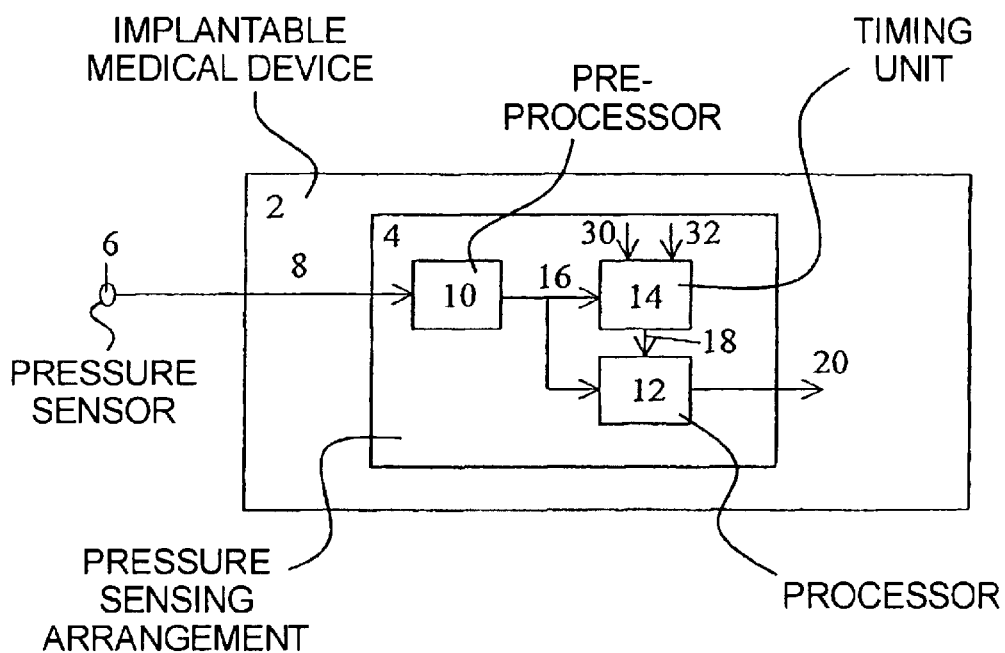
FIG. 1 shows a simplified block diagram of a medical device according to the present invention.

FIG. 1 shows a simplified block diagram of a medical device 2 according to the present invention. The medical device 2 has a pressure sensing arrangement 4 arranged to measure right ventricular pressure of a heart. The pressure sensing arrangement 4 includes a pressure sensor 6 adapted to be positioned in the right ventricle of the heart to measure pressure and to generate a pressure signal 8 in response to the measured pressure. The pressure sensing arrangement 4 also has a pre-processor 10, pressure signal processor 12 and a timing unit 14. The pressure signal processor 12 determines, from the pre-processed pressure signal 16, using diastolic timing signals 18 from the timing unit 14, a diastolic pressure signal representing the ventricular pressure only during the diastolic phase of the heart cycle. One or several threshold values 30, 32 are applied at the timing unit 14 in order to enable the generation of the diastolic timing signals.

Figure 2:
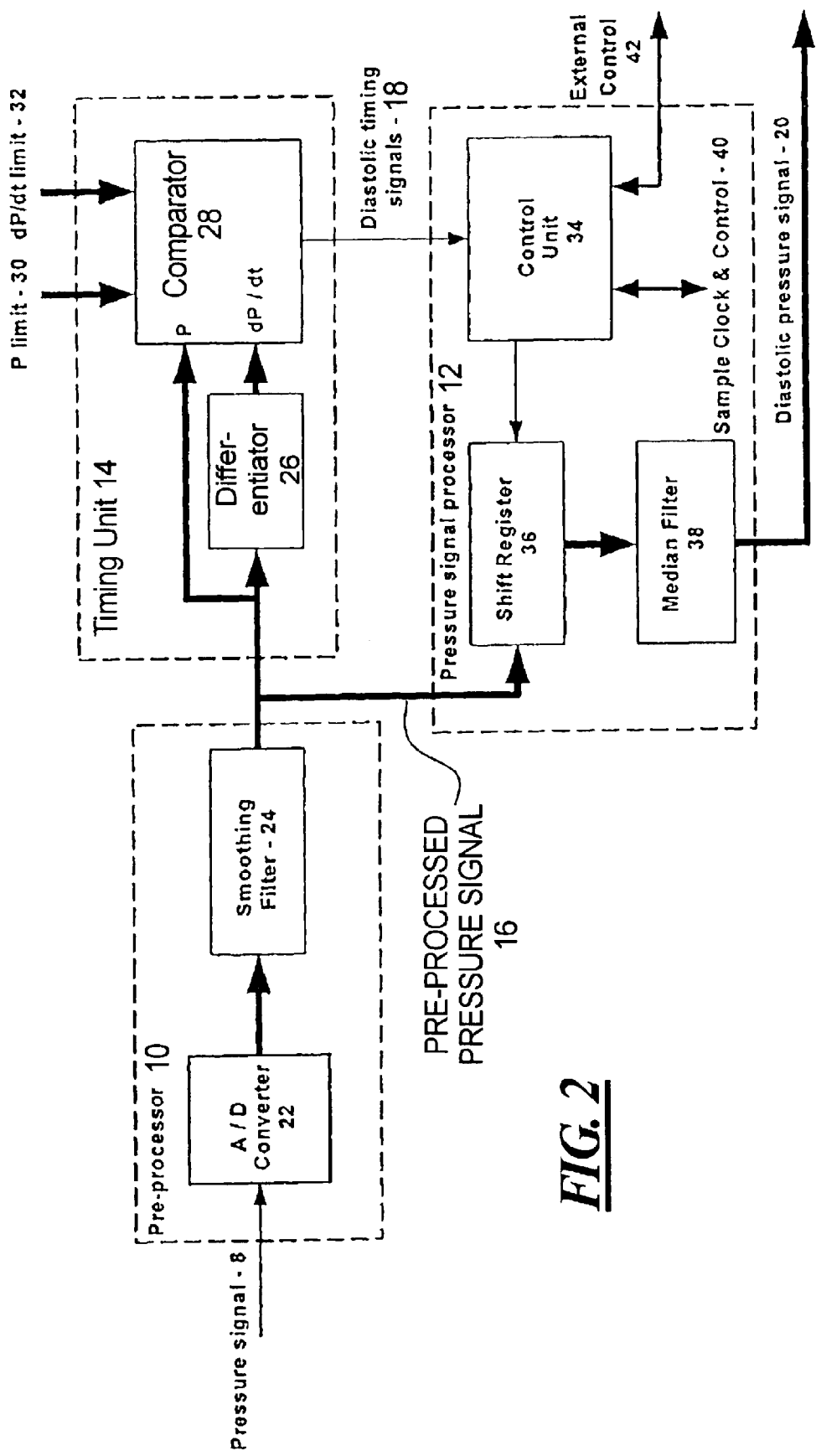
FIG. 2 shows a block diagram of a preferred embodiment of the present invention.

FIG. 2 shows a block diagram of a preferred embodiment of the present invention. The pressure signal 8 is applied to the pre-processor 10 where the signal is analog-to-digital converted in an AND converter 22 and filtered in a smoothing filter 24. In the A/D converter 22 the received pressure signal is sampled by a sampling frequency of 100 Hz. The smoothing filter is a fourth order low-pass filter having a border frequency of 15 Hz.

The A/D converted and filtered signal is applied both to the timing unit 14 and to the pressure signal processor 12.

The timing unit 14 has a differentiator 26 and a comparator 28. The signal from the pre-processor is supplied to both differentiator 26 and the comparator 28 in the timing unit 14. The differentiator 26 differentiates the signal that is supplied to the comparator 28. The comparator 28 is provided with two threshold values, "P limit" 30 and "dP/dt limit" 32, that are preset so that the timing unit 14 generates diastolic timing signals 18 at each of the start and end of the diastolic phase of the heart cycle.

Below are some examples of how the thresholds are selected with references to FIGS. 7–9. In FIG. 10 another approach is illustrated to determine the start and end of the diastolic phase of the heart cycle.

Figure 7:
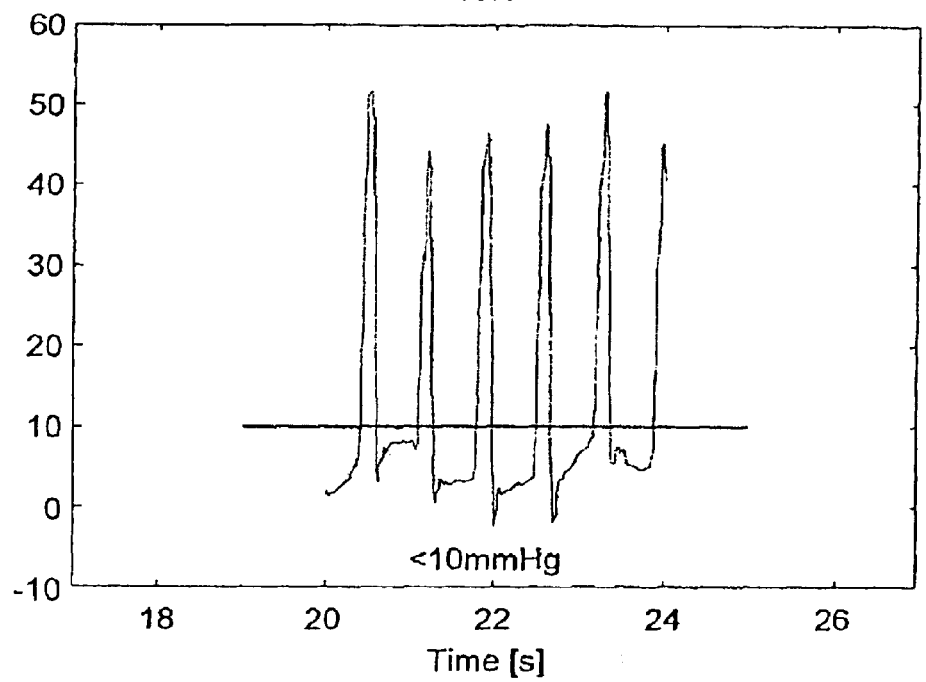
FIG. 7 shows a curve of the amplitude of the right ventricular pressure illustrating how P limit is determined.

FIG. 7 shows the amplitude of the right ventricular pressure (RVP) and a typical P limit of 10 mmHg is marked by the horizontal line. The diastolic phase is identified as the tracings below the line and the start and end points are easily determined as the intersections between the line and the tracing.

Figure 8:
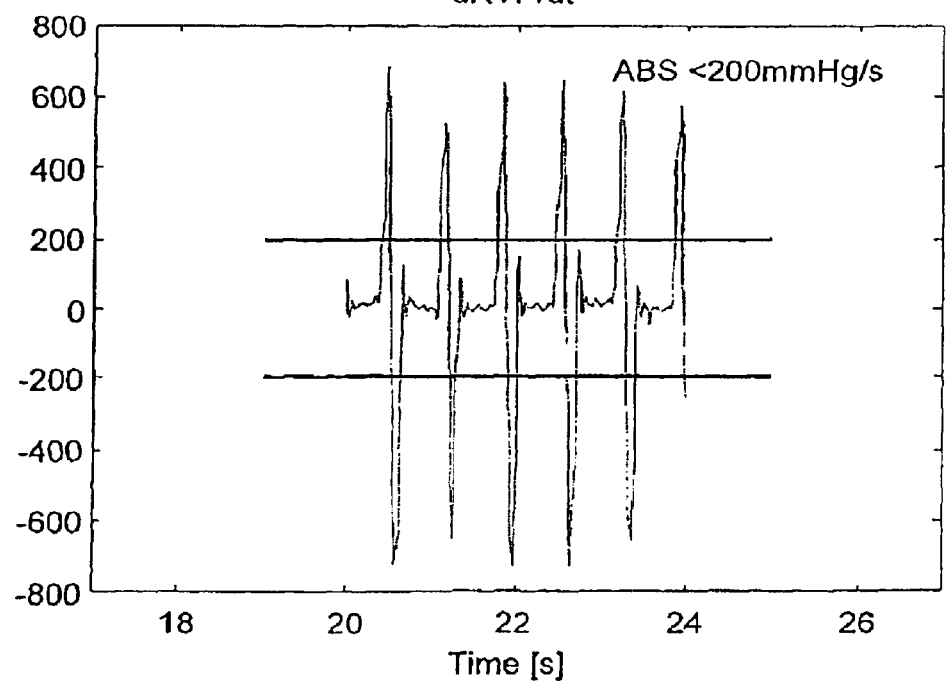
FIG. 8 shows a curve of the amplitude of the right ventricular pressure derivative illustrating how dP/dt limit is determined.

FIG. 8 shows the amplitude of dRVP/dt and a typical dRVP/dt interval for the absolute value of dRVP/dt being less than 200 mmHg/s is marked by horizontal lines. The diastolic phase is identified as the tracings between the lines and the start and end points are then easily determined.

Figure 9:
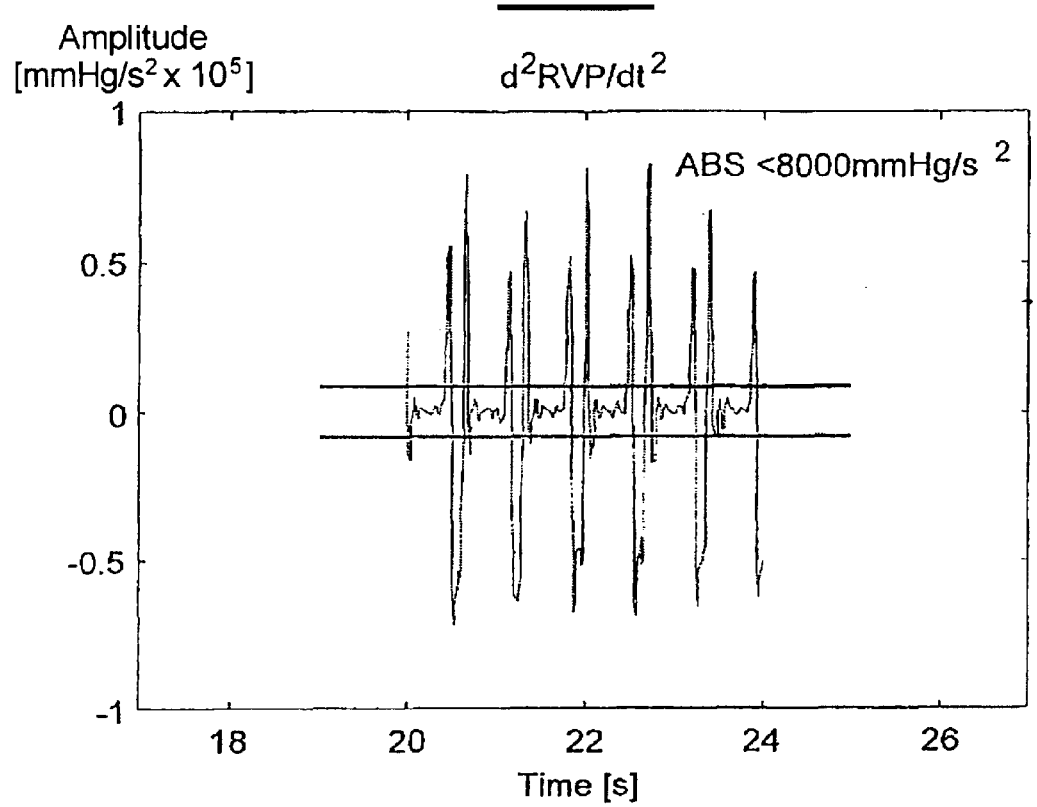
FIG. 9 shows a curve of the amplitude of the right ventricular pressure second derivative illustrating how $d^2P/dt_2$ limit is determined.
Figure 10:
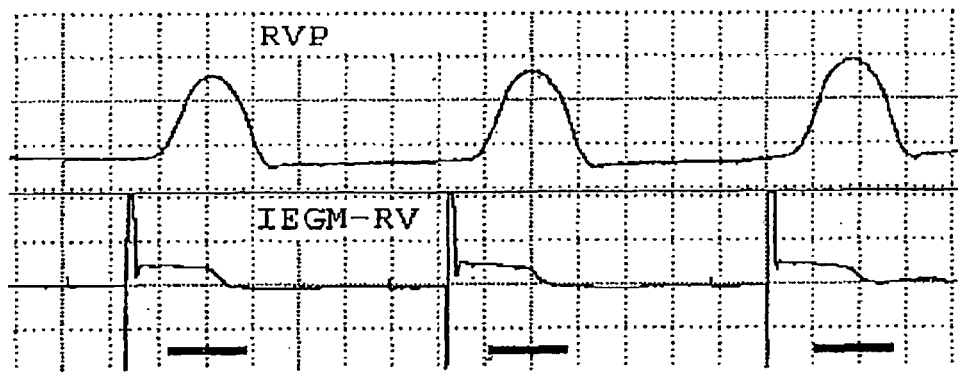
FIG. 10 show curves illustrating an alternative way of determining start and end of diastolic phase.

FIG. 9 shows still another possibility wherein the derivative of the dP/dt is determined and used in combination with the pressure signal (FIG. 7) and/or the derivative of the pressure signal (FIG. 8) as threshold values.

FIG. 10 illustrates a further enhancement where timing information is used obtained from detection of electrical activity of the heart.

FIG. 10 shows schematically how this information may be used:

The upper trace shows the measured pressure (Y-axis line separation being e.g. 20 mm Hg) in the right ventricle and the lower trace (X-axis line separation being e.g. 120 ms) shows the internal EGM measured by a bipolar pacemaker electrode placed in the right ventricle. The heartbeats are detected as the vertical spikes in the IEGM-RV signal. This information can be used to block the pressure detector in for instance the time interval 100–250 ms after the detection. These time intervals are shown as the thick lines in the lower trace as being the systolic time interval.

Again referring to FIG. 2, the diastolic timing signals are applied to a control unit 34 in the pressure signal processor 12 that controls a shift register 36 to which the pre-processed pressure signal 16 is supplied.

The shift register 36 is a First In First Out (FIFO) register where measurement data are shifted in during diastole detection. The register contains only samples of right ventricular pressure (RVP) during diastole. The end of one diastole interval is merged to the beginning of the next interval.

The data registered in the shift register are then supplied to a median filter 38 that generates the diastolic pressure signal 20 which is the median filtered version of the continuously detected diastole intervals. Between the intervals the last data in an interval is hold and a smooth merge to the next (adjacent) diastolic segment (interval) is obtained by using a median filtering technique (see e.g. U.S. Pat. No. 5,871,509). The output diastolic pressure signal is the median value of e.g. the last 9 samples of smoothed pressure signal.

In order to illustrate the benefits of using a median filter 38, FIGS. 6a and 6b show the CVP calculated from the RVP and the RVP without (FIG. 6a) and with (FIG. 6b) using a median filter, respectively. In FIG. 6a the RVP signal is much more erratic whereas in FIG. 6b a smooth transition between the different heart cycles is accomplished.

The control unit 34 controls the different parts of the pressure sensing arrangement by providing sample clock signals and control signals 40 to the preprocessor 10, timing unit 14 and to the shift register 36 and the median filter 38. In order to simplify the illustration of the preferred embodiment in FIG. 2 these clock signals and control signals are not shown. The control unit 34 also communicates with other control units arranged in the medical device 2.

Figure 3:
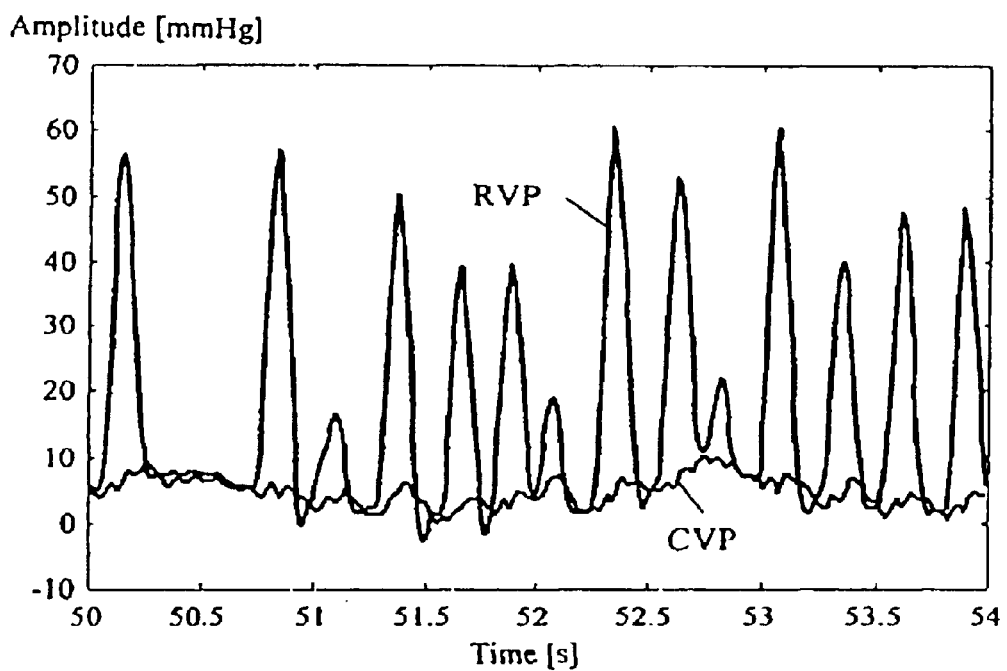
FIG. 3 shows a comparison between measured pressure in the right ventricle (RVP) and measured pressure in the vena cava (CVP).

In order to illustrate the basic principles underlying the present invention FIG. 3 shows a comparison between measured pressure in the right ventricle (RVP) and measured pressure in the vena cava (CVP). As can be seen in FIG. 3 the lower parts of the RVP, the pressure during diastole, essentially coincide with CVP.

Figure 4:
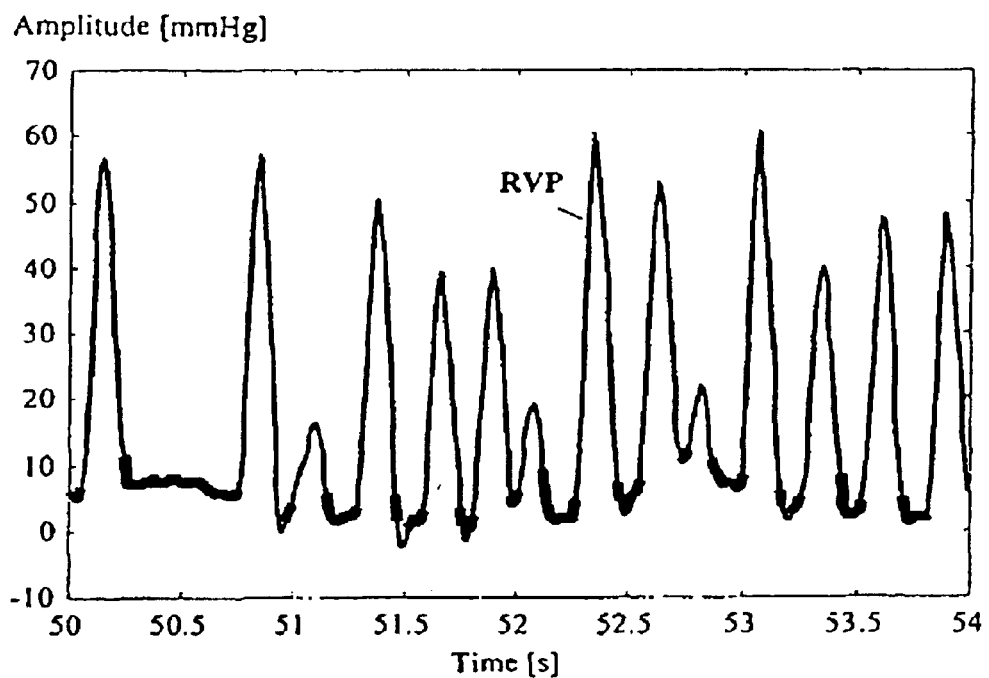
FIG. 4 shows a processed curve of the right ventricular pressure (RVP) illustrating the present invention.

FIG. 4 shows the curve of the right ventricular pressure (RVP), the same as in FIG. 3. In FIG. 4 the two measured pressure curves shown in FIG. 3 have been compared and curve segments where the RVP is within 3 mmHg from the CVP have been marked with a thick line. It is clear from FIG. 4 that the RVP during the diastolic phase of the heart cycle coincides to a high degree with the CVP.

Figure 5:
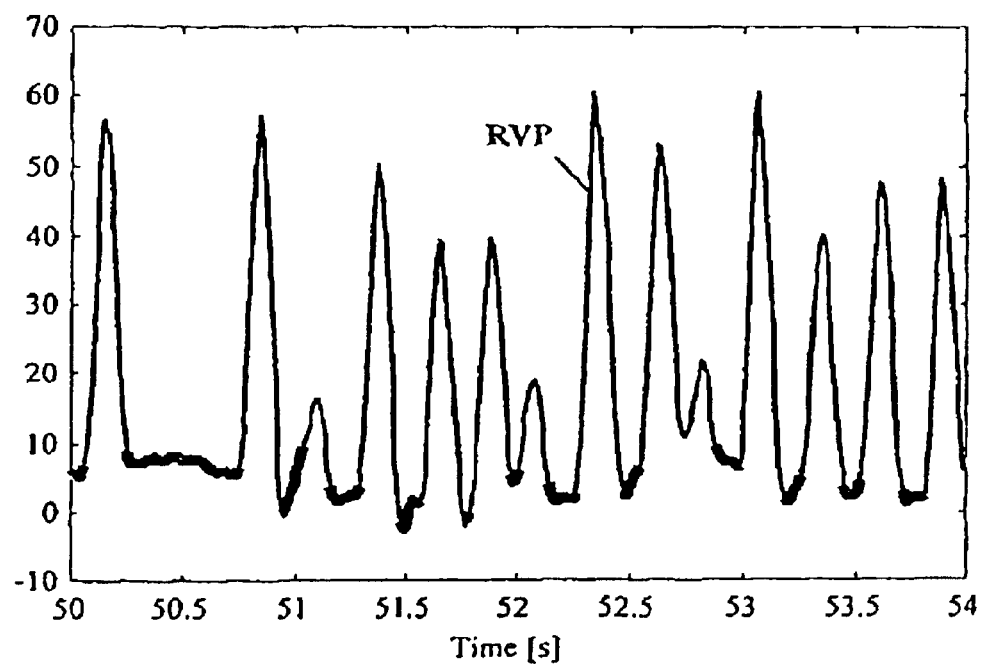
FIG. 5 shows the curve of the right ventricular pressure (RVP) where the diastolic segments of the curve have been determined according to the present invention.

FIG. 5 shows the curve of the right ventricular pressure (RVP), the pressure signal 8 in FIGS. 1 and 2. The pressure signal is supplied to the pressure sensing arrangement 4 of the medical device 2 according to the present invention and a diastolic pressure signal 20 has been generated in response thereto. In FIG. 5 the diastolic segments of the RVP have been marked with a thick line.

Figure 1A:
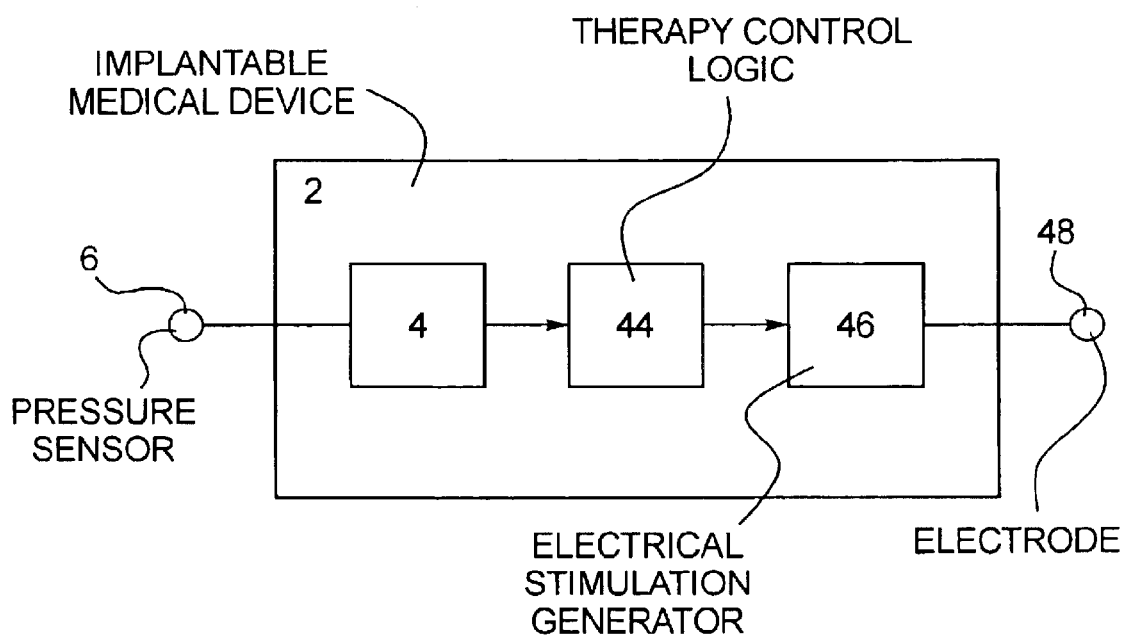
FIG. 1a is a block diagram of a further embodiment of a medical device according to the present invention, for administering electrical stimulation therapy.

In an embodiment of the present invention shown in FIG. 1a, the medical device 2 is an implantable heart stimulator which provides therapy in the form of electrical stimulation. The medical device 2 then, in addition to the pressure sensing arrangement further has a stimulation signal generator and therapy control logic 44. The diastolic pressure signal 20 is applied to the control logic 44 that controls, in response to the diastolic pressure signal, the generation of electrical stimulation from the stimulator signal generator 46. The generated electrical stimulation is supplied to heart tissue via one or more electrode 48 leads in accordance with established stimulation techniques.

The electrical stimulation generator can generate pacing pulses, in which case the therapy control logic 44 is pacing logic, or can generate defibrillation pulses, in which case the therapy control logic 44 is, or includes, fibrillation detection logic, or can generate cardioversion pulses, in which case the therapy control logic is, or includes, arrhythmia detection logic.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable medical device comprising:
   a pressure sensor adapted to be positioned in the right ventricle of a heart, for measuring right ventricular pressure and for generating a pressure signal corresponding to the measured right ventricular pressure;
   a timing unit supplied with said pressure signal which determines, from said pressure signal, diastolic timing signals identifying a beginning and an end of a diastolic phase of the heart; and
   a signal processor connected to the timing unit and also supplied with said pressure signal, said signal processor, using said diastolic timing signals, determining from said pressure signal a diastolic pressure signal representing right ventricular pressure only during the entire diastolic phase of the heart cycle defined by said beginning and said end.

2. An implantable medical device as claimed in claim 1 wherein said timing unit comprises a differentiator which differentiates said pressure signal to obtain a differentiated pressure signal, and a comparator supplied with said pressure signal and said differentiated pressure signal, said timing unit also being supplied with respective threshold values for said pressure signal and for said differentiated pressure signal and comparing said pressure signal and said differentiated pressure signal with the respective threshold values to generate said diastolic timing signals.

3. An implantable medical device as claimed in claim 2 wherein said timing unit comprises a further differentiator which differentiates said differentiated pressure signal to obtain a second differentiated pressure signal, and wherein said timing unit uses said second differentiated pressure signal in combination with said pressure signal as the respective threshold values.

4. An implantable medical device as claimed in claim 2 wherein said timing unit comprises a further differentiator which differentiates said differentiated pressure signal to obtain a second differentiated pressure signal, and wherein said timing unit uses said second differentiated pressure signal in combination with the differentiated pressure signal as the respective threshold values.

5. An implantable medical device as claimed in claim 2 wherein said timing unit comprises a further differentiator which differentiates said differentiated pressure signal to obtain a second differentiated pressure signal, and wherein said timing unit uses said second differentiated pressure signal in combination with the pressure signal and the differentiated pressure signal as the respective threshold values.

6. An implantable medical device as claimed in claim 1 wherein said signal processor generates said diastolic pressure signal substantially continuously during an entirety of said diastolic phase.

7. An implantable medical device as claimed in claim 1 wherein said signal processor comprises a median filter which generates a smoothed combination of respective diastolic pressure signals from a plurality of successive heart cycles.

8. An implantable medical device as claimed in claim 1 further comprising an electrical stimulation generator which emits electrical signals comprising stimulation therapy, and therapy control logic supplied with said diastolic pressure signal for controlling said electrical stimulation generator to administer said stimulation therapy dependent on said diastolic pressure signal.

\* \* \* \* \*